(12) United States Patent
Zangmeister et al.

(10) Patent No.: US 8,962,345 B2
(45) Date of Patent: Feb. 24, 2015

(54) METHOD OF CHARACTERIZING GLYCANS ATTACHED TO GLYCOPROTEINS

(75) Inventors: Rebecca A. Zangmeister, Gaithersburg, MD (US); Germarie Sanchez-Pomales, Gaithersburg, MD (US); Todd A. Morris, Selinsgrove, PA (US); Michael J. Tarlov, Bethesda, MD (US)

(73) Assignees: The United States of America as represented by the Secretary of Commerce, Washington, DC (US); The National Institute of Standards and Technology, Gaithersburg, MD (US)

( * ) Notice: Subject to any disclaimer, the term of this patent is extended or adjusted under 35 U.S.C. 154(b) by 819 days.

(21) Appl. No.: 13/112,822

(22) Filed: May 20, 2011

(65) Prior Publication Data

US 2011/0287559 A1 Nov. 24, 2011

Related U.S. Application Data

(60) Provisional application No. 61/346,928, filed on May 21, 2010.

(51) Int. Cl.
*G01N 33/543* (2006.01)
*G01N 33/68* (2006.01)

(52) U.S. Cl.
CPC ........ *G01N 33/6854* (2013.01); *G01N 2400/02* (2013.01)
USPC ............. 436/518; 435/7.1; 436/501; 436/523

(58) Field of Classification Search
None
See application file for complete search history.

(56) References Cited

U.S. PATENT DOCUMENTS

| | | | |
|---|---|---|---|
| 5,362,480 A * | 11/1994 | Au et al. .......................... | 424/54 |
| 5,888,757 A | 3/1999 | Kuranda | |
| 5,965,457 A | 10/1999 | Magnani | |
| 6,197,599 B1 | 3/2001 | Chin et al. | |
| 7,056,678 B1 | 6/2006 | Markman | |
| 7,132,251 B1 | 11/2006 | Markman et al. | |
| 7,138,371 B2 * | 11/2006 | DeFrees et al. .............. | 424/85.2 |
| 7,407,773 B2 | 8/2008 | Markman et al. | |
| 7,455,979 B2 | 11/2008 | Markman | |
| 7,741,061 B2 | 6/2010 | Markman | |
| 2008/0145441 A1 * | 6/2008 | Penades et al. ............... | 424/499 |
| 2009/0325199 A1 * | 12/2009 | Geddes ......................... | 435/7.23 |
| 2010/0216162 A1 * | 8/2010 | Meyr et al. .................... | 435/7.9 |
| 2012/0164666 A1 * | 6/2012 | Mullen ......................... | 435/7.37 |

OTHER PUBLICATIONS

Maesaki, Drug Delivery System of Anti-fungal and Parasitic Agents, Current Pharmaceutical Design, 2002, 8, pp. 433-440.*
Sanchez-Pomales et al., A Lectin-Based Gold Nanoparticle Assay for Probing Glycosylation of Glycoproteins, Biotechnology and Bioengineering, vol. 109, No. 9, Sep. 2012, pp. 2240-2249.*
Kim et al., High-Throughput Screening of Glycan-Binding Proteins using Miniature Pig Kidney N-Glycan immobilized Beads, Chemistry & Biology 15, Mar. 2008, pp. 215-223.*

* cited by examiner

*Primary Examiner* — Gary W Counts
(74) *Attorney, Agent, or Firm* — Steve Witters; Witters & Associates

(57) ABSTRACT

A method of characterizing glycans attached to glycoproteins is disclosed herein. The method comprises a first step of immobilizing the glycoproteins on colloidal particles forming glycoprotein/colloidal particles. The glycans on the glycoproteins may then be characterized, for example the composition and/or structure of glycans may be characterized or the glycans attached to proteins may be identified. Characterization may be accomplished by either binding the glycoprotein/colloidal particles with one or more binding agents and assessing the aggregation of the glycoprotein/colloidal particles or by cleaving glycans from the glycoprotein/colloidal particles with a cleaving agent and analyzing the glycans.

13 Claims, 12 Drawing Sheets

Legend:

= Au NPs   = mAb   = mAb-Au NP conjugate

= Binding Lectin (e.g. WGA, Con A)    = Glycan

METHOD OF CHARACTERIZING GLYCANS ATTACHED TO GLYCOPROTEINS

CROSS-REFERENCE TO RELATED APPLICATIONS

This application claims the benefit of U.S. Provisional Application No. 61/346,928, filed May 21, 2010.

STATEMENT REGARDING FEDERALLY SPONSORED RESEARCH OR DEVELOPMENT

This work is funded by the National Institute of Standards and Technology under the U.S. Department of Commerce.

FIELD OF THE INVENTION

This invention relates to methods for characterizing the composition and/or structure of glycans or identifying glycans attached to proteins, i.e., glycoproteins.

BACKGROUND

The background information is believed, at the time of the filing of this patent application, to adequately provide background information for this patent application. However, the background information may not be completely applicable to the claims as originally filed in this patent application, as amended during prosecution of this patent application, and as ultimately allowed in any patent issuing from this patent application. Therefore, any statements made relating to the background information are not intended to limit the claims in any manner and should not be interpreted as limiting the claims in any manner.

Glycosylation of proteins is an important aspect of protein therapeutics. For example, many Food and Drug Administration (FDA) approved protein therapeutics, and those in clinical trials, are glycoproteins. A majority of FDA approved protein therapeutics may be glycosylated. Glycoproteins are proteins that have oligosaccharide chains or glycans attached to one or more sites on the polypeptide backbone. Glycosylation is the enzymatic linking of sugar molecules to produce oligosaccharides or glycans covalently attached to the protein. This process may result in significant heterogeneity in the composition and structure of attached glycans. This pattern of glycosylation may be crucial in biopharmaceutical development and manufacturing since it may influence binding, clearance, immunogenicity, and mechanism of action of the protein therapeutic.

Therefore, the glycan profile of the protein may need to be carefully monitored to ensure compliance to quality control standards. Typically, the determination of glycan profiles may be achieved by enzymatic cleavage of the glycans from the protein followed by chromatographic or mass spectrometric characterization. Although these methods may provide characterization of glycan structure, they may be time consuming, require expert interpretation, and may not be easily used for monitoring glycan profile changes during a production run in a manufacturing facility. For example, current methods for glycan characterization or methods of characterizing and/or identifying glycoproteins may be time consuming, on the order of 24 hrs or greater, and/or labor intensive. A less time consuming screening method for glycan composition may aid the industry by allowing near real time glycosylation monitoring during upstream processing, i.e., in a bioreactor, and also for bioprocess development.

Monoclonal antibodies (mAbs) are a particularly important therapeutic class because they are a fast growing class of protein therapeutic. All mAbs are glycosylated and the structure and composition of these sugar structures may be critical to their efficacy and safety. Currently, nearly all licensed therapeutic mAbs have been of the IgG (immunoglobulin G) class. The oligosaccharides or glycans of mAbs may be attached to two specific amino acid residues in the stem region of the antibody. In the IgG class, glycans (or oligosaccharides) may be covalently attached at asparagine 297 of each heavy chain in the Fc region of the mAb. The glycan component may affect the solubility, stability, immunogenicity and effector function of mAbs. It therefore may be essential to characterize and control the glycosylation of therapeutic mAbs.

The production of therapeutic mAbs with a consistent glycosylation pattern may currently present a considerable challenge to the biopharmaceutical industry. As a result, product release may require extensive characterization of oligosaccharide or glycan composition to ensure product quality and consistency. For example, chromatography or mass spectrometry are typically used to analyze the glycan content of mAbs. These methods of analysis of glycans may be time-consuming, may involve enzymatic cleavage of the glycans prior to analysis, and may require expensive instrumentation and highly-trained personnel.

There is a need for a method of characterizing glycans attached to glycoproteins that may overcome at least some of the deficiencies of the prior art.

SUMMARY

In at least one aspect of the present disclosure, a method of characterizing glycans attached to glycoproteins comprises the steps of immobilizing the glycoproteins on colloidal particles, forming glycoprotein/colloidal particles, and one of steps b) and steps c). Step b) comprises binding the glycoprotein/colloidal particles with a binding agent; assessing the aggregation of the glycoprotein/colloidal particles; and characterizing the glycans. Step c) comprises cleaving glycans from the glycoprotein/colloidal particles with a cleaving agent and analyzing and characterizing the glycans.

In at least one other aspect of the present disclosure, a method of characterizing glycans attached to glycoproteins comprises the steps of: a) immobilizing the glycoproteins on colloidal particles forming glycoprotein/colloidal particles; b) binding the glycoprotein/colloidal particles with a binding agent; c) assessing the aggregation of the glycoprotein/colloidal particles; and d) characterizing the glycans.

In at least one additional aspect of the present disclosure, a method of characterizing glycans attached to glycoproteins comprises the steps of: a) mixing the glycoproteins with colloidal particles; b) forming glycoprotein/colloidal particles; b) binding the glycoprotein/colloidal particles; and d) characterizing the glycans.

BRIEF DESCRIPTIONS OF THE DRAWINGS

The following figures, which are idealized, are not to scale and are intended to be merely illustrative and non-limiting.

Figure 6:
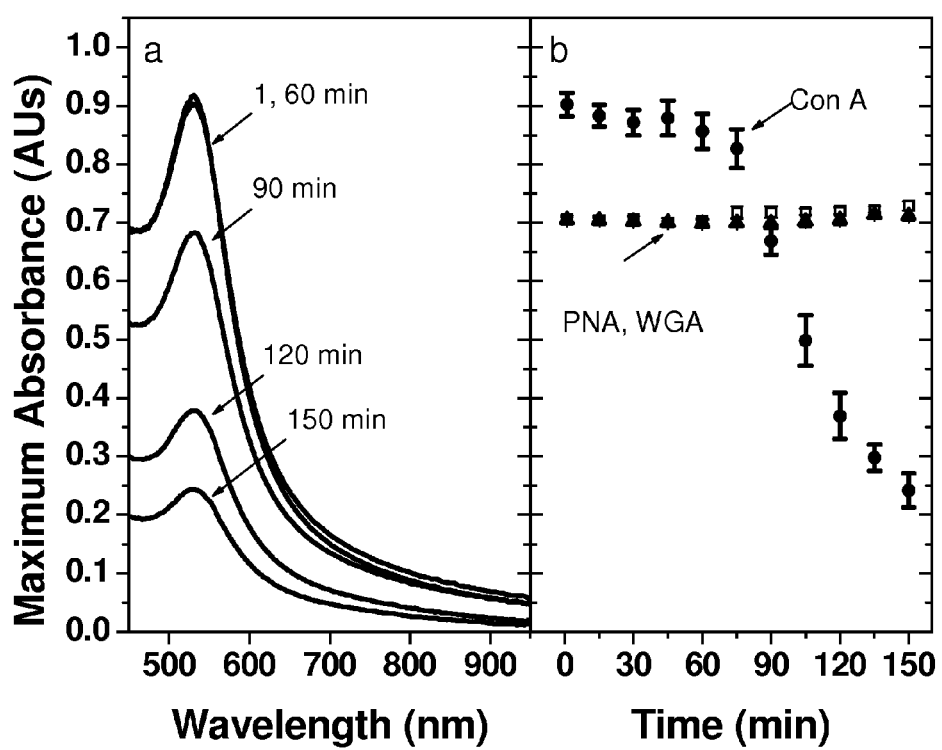
Figure 7A:
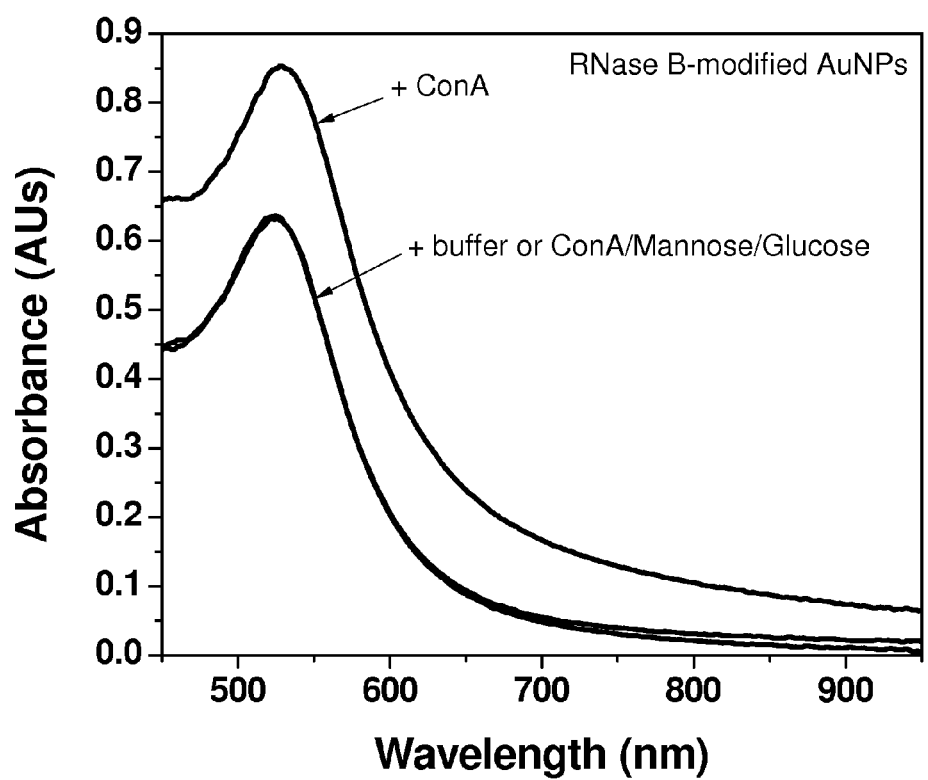
Figure 7B:
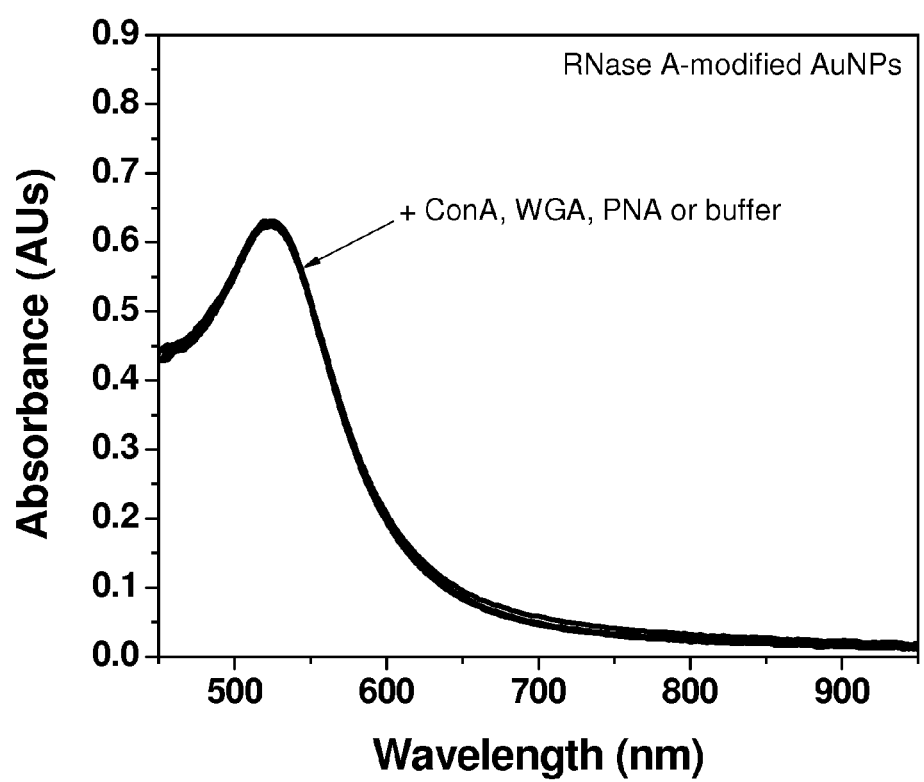
Figure 8A:
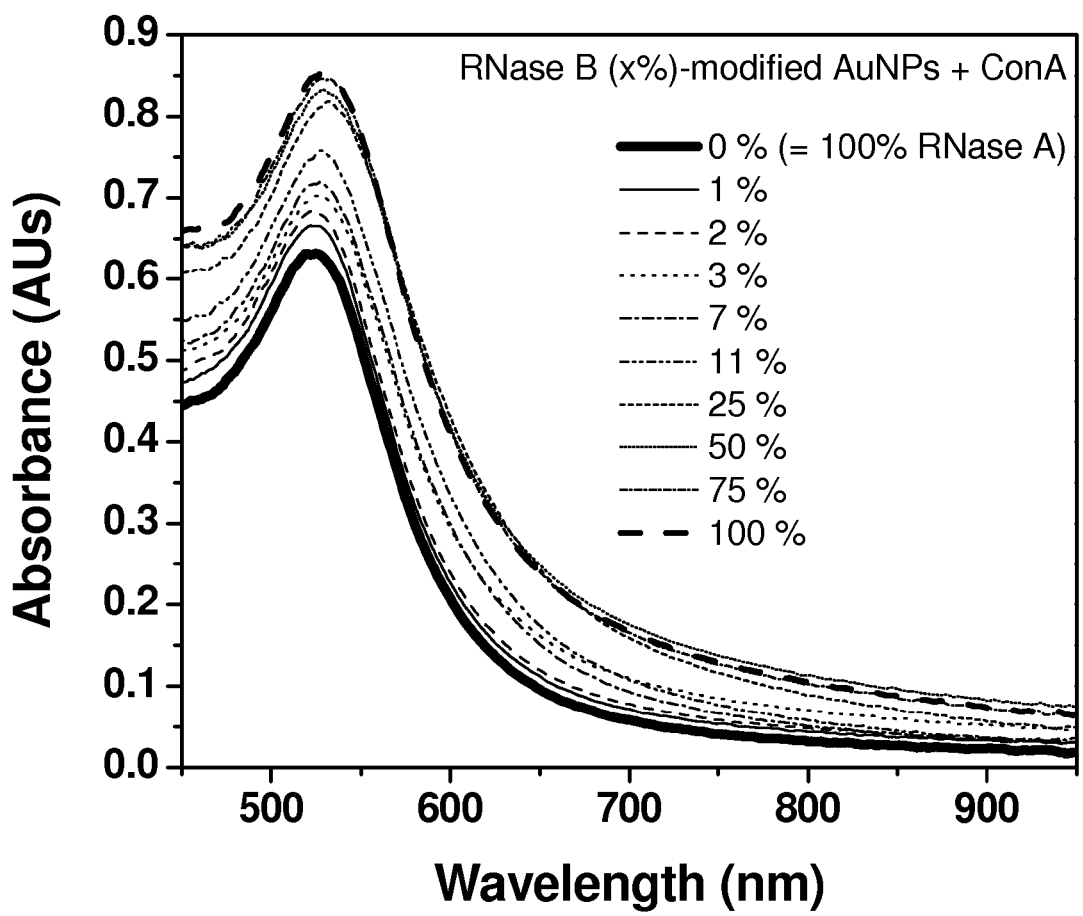
Figure 8B:
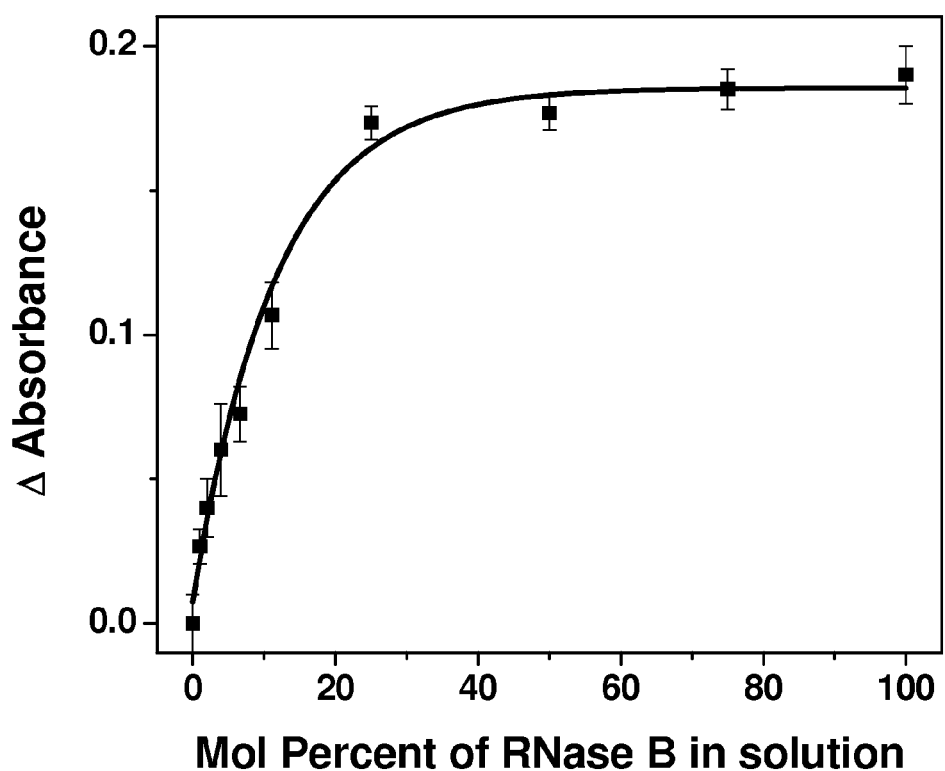
Figure 9:
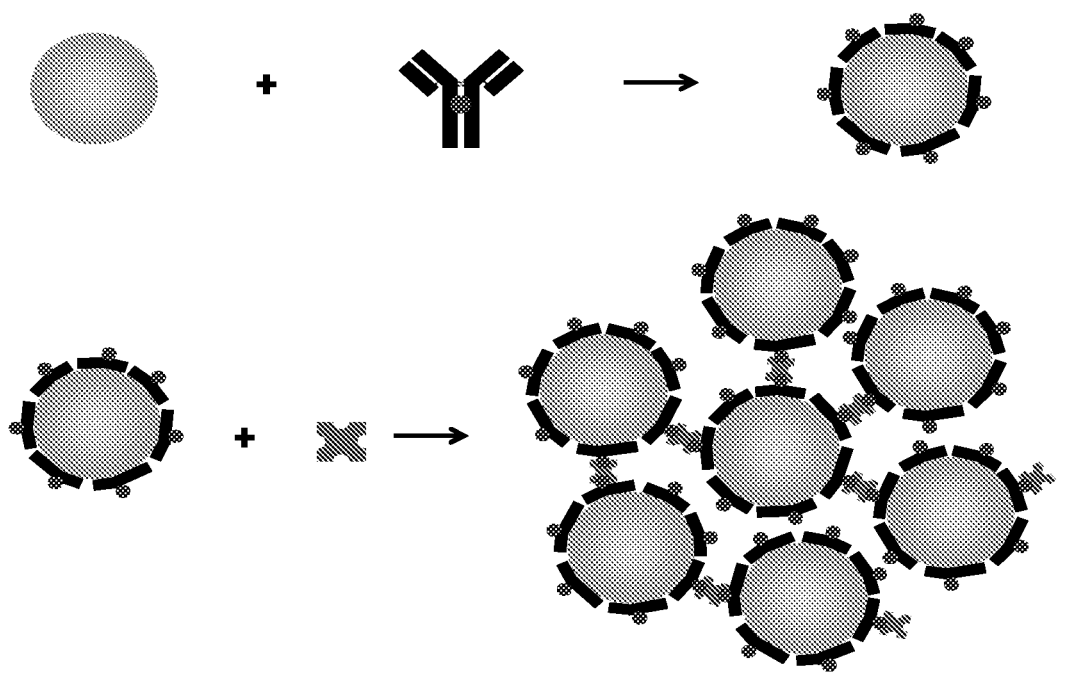
Figure 9:
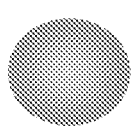
Figure 9:
Figures 10A, 10B:
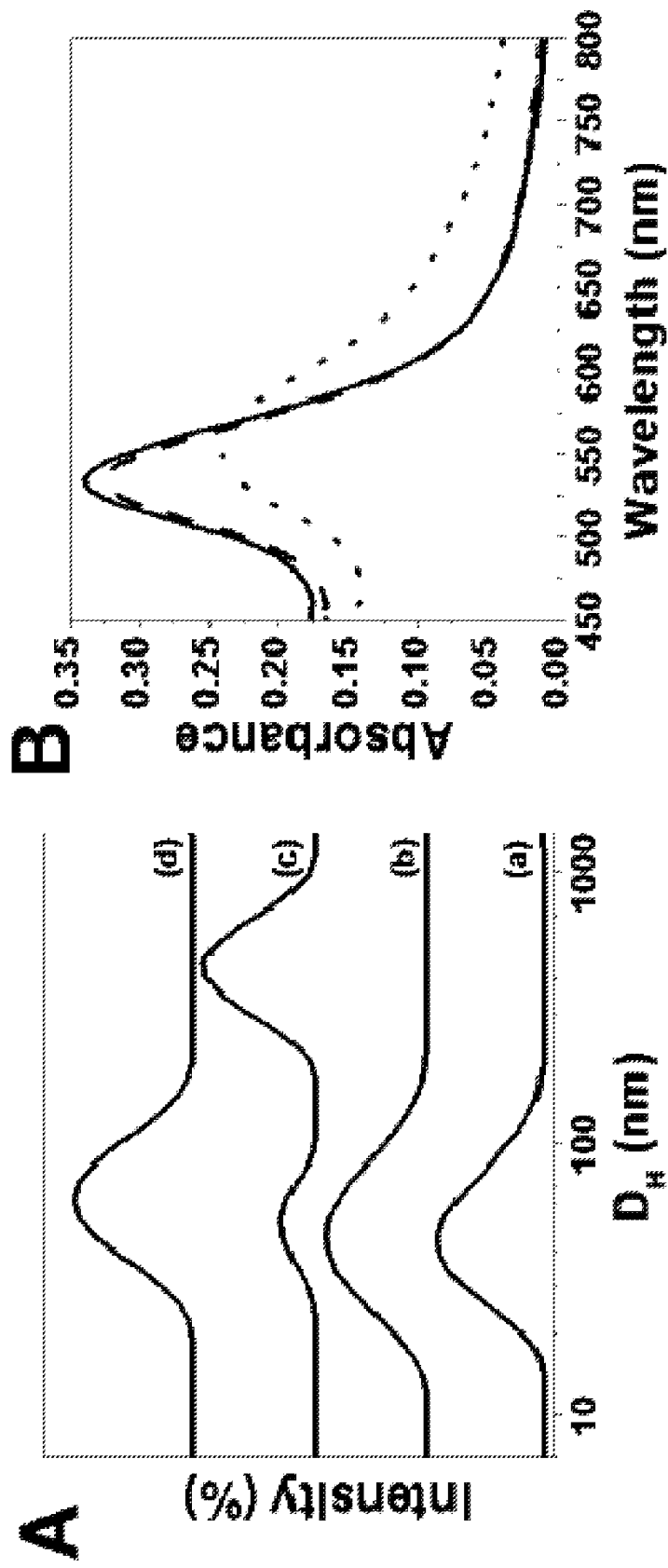
Figures 11A, 11B:
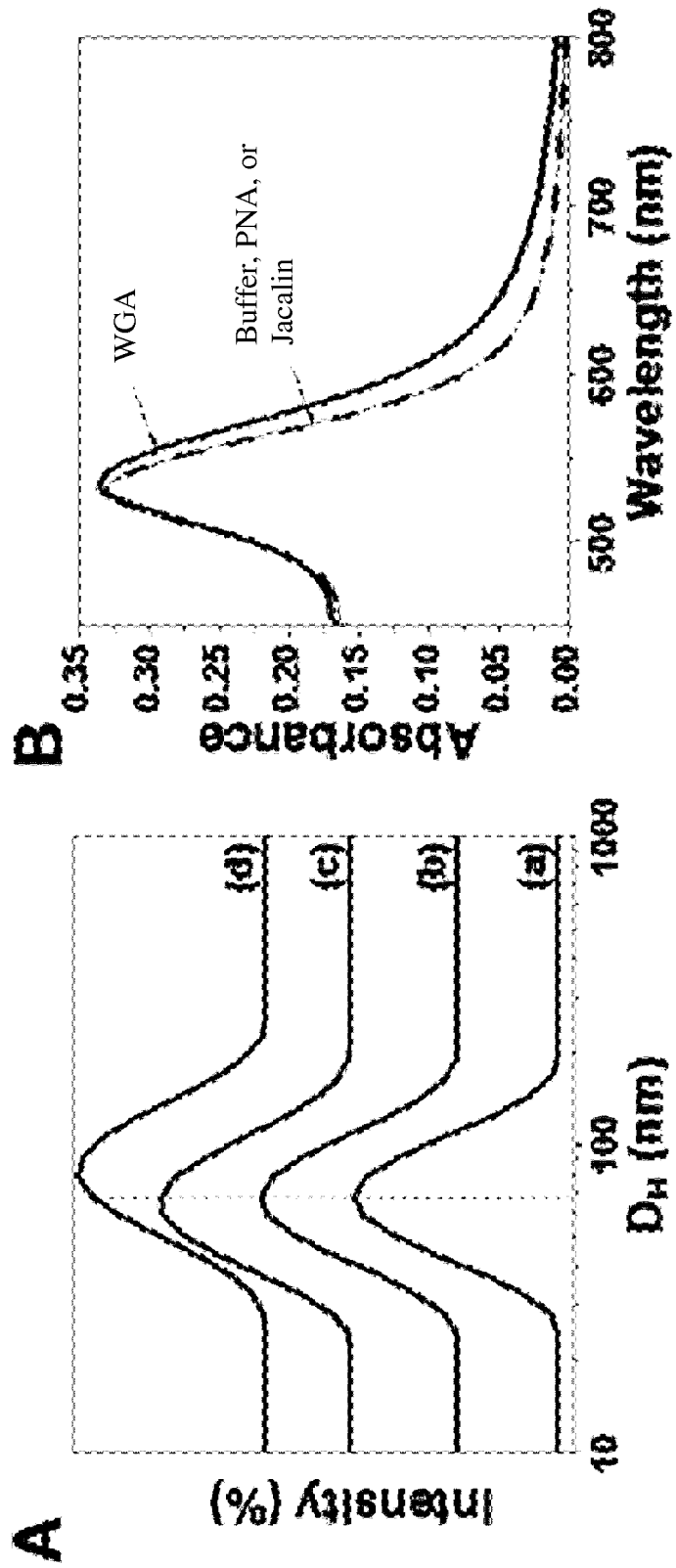

FIG. 6 shows a UV-Vis spectra of RNase B-modified gold nanoparticles 1, 60, 90, 120, and 150 min after introduction of Con A and change in maximum absorbance (ca. 529 nm for Con A and ca. 525 nm for WGA or PNA) with time for RNase B-modified gold nanoparticles after exposure to Con A(●), WGA(▲), or PNA (□) wherein error bars represent one standard deviation above and below the mean of at least 3 replicates;

FIG. 7A shows UV-Vis spectra of RNase B-modified gold nanoparticles approximately 1 min after the addition of Con A with (bottom trace) and without (top trace) the addition of an excess inhibitory sugar mixture of mannose and glucose;

FIG. 7B shows UV-Vis spectra of RNase A-modified gold nanoparticles approximately 1 min after the addition of Con A, WGA, PNA, or buffer. The nanoparticle concentration was the same for all experiments;

FIG. 8A shows UV-Vis spectra of RNase B-modified gold nanoparticles approximately 1 min after the addition of Con A at various mole percent of RNase B wherein the final concentration of Con A was 50 µg/mL;

FIG. 8B shows change in maximum absorbance measured at ca. 529 nm for Con A as a function of RNase B solution mole percent wherein error bars represent one standard deviation above and below the mean of at least 3 replicates;

FIG. 9 shows a schematic of lectin-based aggregation of mAb-Au NP conjugates;

FIG. 10A shows DLS diameter results for the Rituxan®-Au NP conjugates before (a) and two hours after the addition of PNA (b), WGA (c) and WGA/GlcNAc (d);

FIG. 10B shows UV-visible spectra of Rituxan®-Au NP conjugates after two hours in buffer (solid line) and in the presence of PNA (dashed line) and WGA (dotted line);

FIG. 11A shows DLS diameter results for the Rituxan®-Au NP conjugates before (a) and approximately one minute after the addition of PNA (b), Jacalin (c) and WGA (d); and FIG. 11B shows UV-visible spectra of Rituxan®-Au NP conjugates approximately one minute after dilution with buffer (borate, pH=7.5), or upon addition of PNA, Jacalin and WGA lectins.

DETAILED DESCRIPTION

Methods for preparing, characterizing and/or identifying the composition and/or structure of oligosaccharides or glycans attached to proteins, i.e., glycoproteins, are disclosed herein. Particular materials, constituents, amounts thereof, conditions (e.g. temperature, pH, etc.), process equipment, reaction times, analytical equipment, and other parameters are disclosed herein as by way of illustration or example and should not be construed to unduly limit this disclosure. For example, selected glycoproteins and selected colloidal particles are disclosed, by way of example only, and their selection shall not be construed to limit the claims herein.

The present disclosure is directed to a method for preparing, characterizing and/or identifying the composition and/or structure of oligosaccharides or glycans attached to proteins. The method may comprise the steps of: a) immobilizing glycoproteins on colloidal particles and one of Steps b) and c). Step b) comprises binding the glycoprotein/colloidal particles with a binding agent such as sugar binding proteins (e.g. lectins and antibodies), nucleic acids, and polymeric materials, and assessing the aggregation of the glycoprotein/colloidal particles. The assessment of the aggregation of the glycoprotein/colloidal particles may provide data for screening, characterizing and/or identifying the composition and/or structure of oligosaccharides or glycans attached to the protein. Step c) comprises cleaving the glycans or oligosaccharides from the immobilized glycoprotein, thereby releasing glycans for further analysis by chromatography or mass spectrometry, for example. In at least one aspect, glycoproteins are immobilized by absorbing them onto gold nanoparticles in step a).

The method may include the steps of immobilizing glycoproteins on colloidal particles and mixing the glycoprotein/colloidal particles with one or more binding agents such as sugar binding proteins, nucleic acids, polymeric materials, and combinations thereof, and assessing the aggregation of the glycoprotein/colloidal particles. The assessment may be performed with an optical assay or size increase measurement for characterizing and/or identifying and/or screening oligosaccharides attached to the protein. Alternatively, glycans or oligosaccharides may be cleaved from the immobilized glycoproteins, thereby releasing oligosaccharides for further analysis by chromatography or mass spectrometry, for example.

In at least one aspect of the present disclosure, assays, for example binding agent based assays, may hold promise as a simple, inexpensive, and rapid alternative for glycosylation screening of protein drugs and for clinical diagnostic applications. Rapid assays based on binding agents such as lectin (i.e. carbohydrate binding protein), sugar binding proteins, nucleic acids, polymeric materials, other binding agents as are known in the art, and combinations thereof, may provide a relatively simple, fast and/or inexpensive alternative for glycosylation screening of therapeutic mAbs, and may be amenable to in-process control monitoring.

Selected glycoproteins, specifically, but not necessarily limited to, polyclonal or monoclonal antibodies, may spontaneously and strongly adsorb on nanoparticles, for example metallic and non-metallic nanoparticles, such as gold, silver, magnetic, non-magnetic, core-shell, polystyrene, carbon nanotubes, and combinations thereof. The relatively hydrophilic oligosaccharide structures (also known as carbohydrates, sugars, or glycans) of the adsorbed glycoprotein may then be presented to an aqueous solution for potential probing by binding or cleaving reagents.

In at least one aspect of the present disclosure, glycoprotein/gold colloid conjugates may serve as the basis for a spectrophotometric, lectin-based assay to characterize or assess the composition and/or structure of the oligosaccharides of the glycoprotein. Lectins are oligosaccharide binding proteins that may recognize and bind mono- and oligosaccharides reversibly and with high specificity. In addition, each lectin molecule may typically contain two or more carbohydrate-combining sites (i.e., they may be di- or polyvalent). Therefore, when an appropriate lectin is added to a solution containing glycoprotein/gold colloid conjugates, the lectin may recognize and bind with the oligosaccharides that project out from the surface and cause cross-linking of the glycoprotein/gold colloid conjugates. Because the optical properties of the colloids, gold for example, may be sensitive to interparticle separation distance, cross-linking may lead to a change in color or scattered light that may be detected visually, spectrophotometrically, or by scattering measurements (e.g. dynamic light scattering). Furthermore, the use of multiple lectins may allow multiplexed measurements of different glycoforms. For example, a different lectin solution may be contained in each well of a microtiter plate and small aliquots of glycoprotein/gold colloid solution may be pipetted into each well. Because each lectin may exhibit different selectivity depending on the oligosaccharide composition and structure, different color or spectral changes may be exhibited for each well. The resulting spectral changes may constitute a fingerprint for a particular glycosylation of the glycoprotein.

In a second aspect of the present disclosure, colloids, such as gold nanoparticles, may be added to a solution containing a glycoprotein and the glycoprotein may spontaneously adsorb to the colloid surface thereby resulting in presentation of the oligosaccharides for cleavage by an appropriate cleaving agent such as an enzyme or chemical agent. A cleaving agent is an essentially sequence-specific agent that cleaves the saccharide chain at its recognition sequence. Cleaving agents as known in the art, for example, e.g., PNGase F, glycosidases, including exo- and endoglycosidases, and glycosyltransferases, may be used in the presently disclosed method. Also, chemical reagents that are essentially sequence-specific and capable of cleaving a glycosidic bond may serve as cleaving agents. One or more cleaving agents may be used.

Glycoproteins are often immobilized on hydrophobic surfaces to effect cleavage of the protein's glycans. Advantages of immobilization on particle surfaces may include faster immobilization due to higher mass transport rates, higher surface areas, and improved steric accessibility to oligosaccharides which may be due to surface curvature, which may result in faster enzymatic cleavage. A faster immobilization of glycoproteins may help to avoid complex coupling chemistries which may in turn help to avoid additional assay steps.

Figure 1:
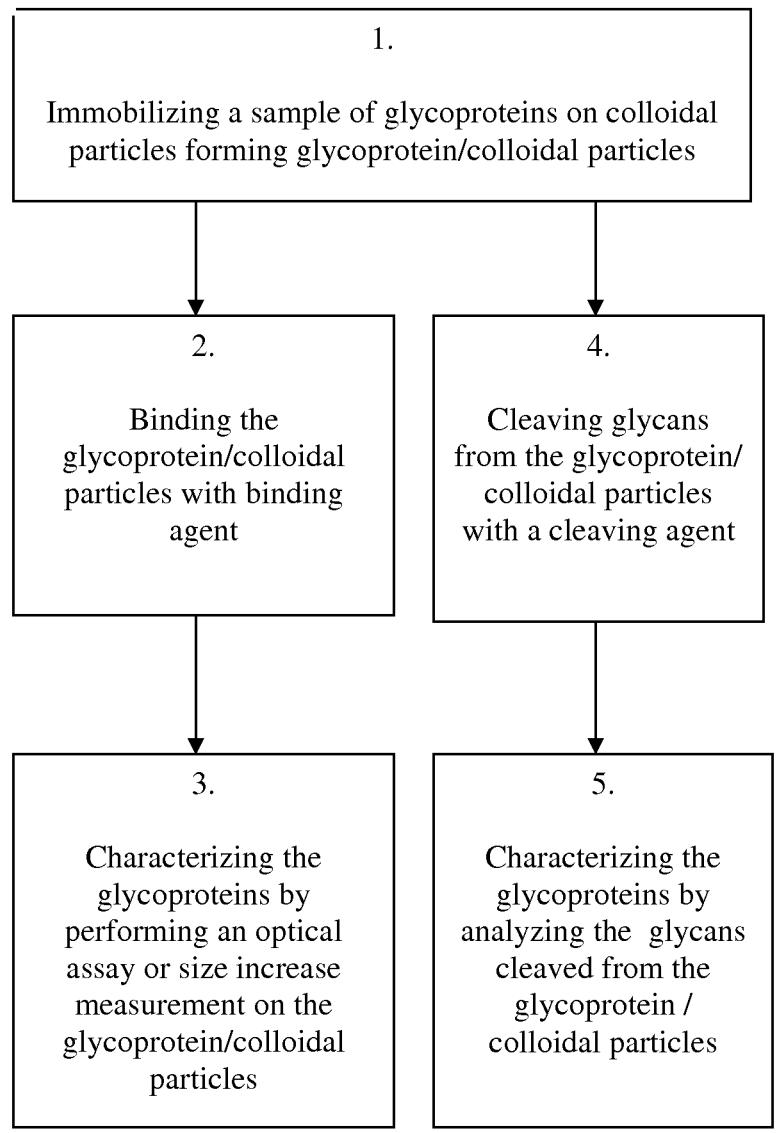
FIG. 1 is a flowchart that shows methods of characterizing the composition and/or structure of glycans or identifying glycans attached to proteins, i.e., glycoproteins of the present disclosure.
Figure 2:
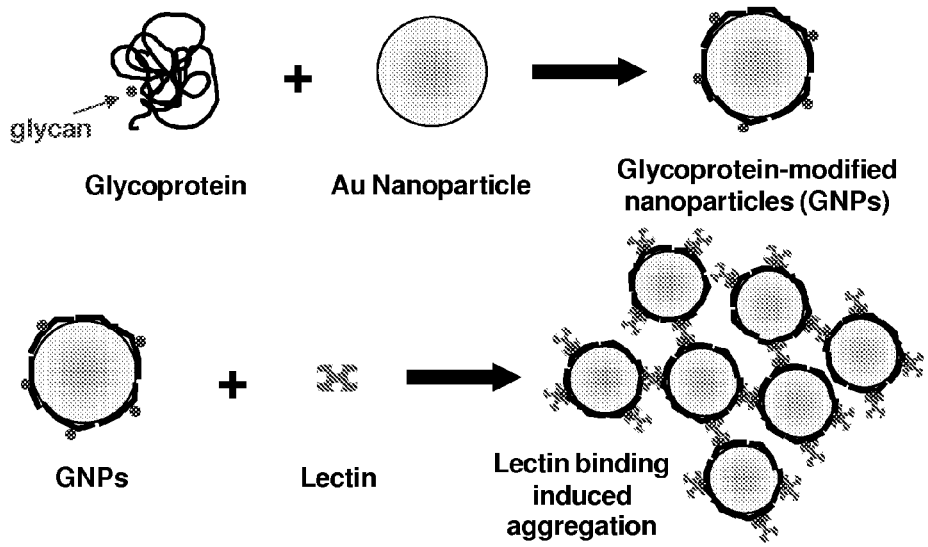
FIG. 2 is a schematic representation of the rapid glycan assay.

FIG. 1 is a flowchart that shows method Steps 1-5 for characterizing the composition and/or structure of glycans and/or identifying glycans. Step 1 comprises immobilizing a sample of glycoproteins on colloidal particles forming glycoprotein/colloidal particles. The colloidal particles may have an average size of less than 1000 nm in at least one dimension, in one nanometer increments. For example, colloidal particles may have an average diameter of less than or equal to about 50 nanometers, less than or equal to about 30 nanometers, less than or equal to about 10 nanometers, or less. The colloidal particles may comprise metallic and/or non-metallic nanoparticles such as gold, silver, magnetic, non-magnetic, core-shell, polystyrene, carbon nanotubes, other materials known in the art configured to bind with glycoproteins, and combinations thereof.

In at least one aspect, for example, colloidal particles may comprise metallic or non-metallic nanoparticles including gold, silver, magnetic, non-magnetic, core-shell, polystyrene, carbon nanotubes, and combinations thereof. For example, colloidal particles may comprise gold nanoparticles (Au NPs). The Au NPs may be stabilized, for example citrate-stabilized. For example, colloidal particles may comprise citrate-stabilized gold nanoparticles having concentration of about $5.7 \times 10^{12}$ particles/mL and an average diameter of about 10 nm. In at least one other aspect, for example, colloidal particles may comprise citrate-stabilized gold nanoparticles, having an average diameter of about 30 nm and a concentration of about $2.0 \times 10^{11}$ particles/ml. pH, temperature, and other conditions of solutions may be adjusted and/or maintained. For example, in at least one aspect, the pH of a solution of citrate-stabilized gold nanoparticles, having a diameter of about 10 nm for example, may be raised to a pH of about 10 by adding 0.1 mol/L NaOH, as measured with pH test strips.

In at least one aspect, the step of immobilizing glycoproteins on colloidal particles of Step 1 may be carried out by first dissolving the protein in water. The concentration of protein in water may be made as desired. In at least one aspect, the concentration of protein in water may be made about 1 mg/mL, for example. Glycoproteins may be selected from the group consisting of polyclonal antibodies, monoclonal antibodies, and combinations thereof. For example, in at least one aspect, the protein may comprise Ribonuclease B (RNase B, from bovine pancreas, >80%), the concentration of which may result in saturation of protein coverage as determined by analytical ultracentrifugation (AUC) analysis. The protein solution may then be added to the gold nanoparticle solution at a desired volume ratio. For example, the protein solution may then be added to the gold nanoparticle solution at a ratio of about 1:10, for example, yielding a final protein concentration of about 100 μg/mL when mixed with the nanoparticles. The solution may then be mixed and allowed to incubate at a desired temperature for a desired period of time. For example, the mixture may be allowed to incubate at room temperature for at least about 30 minutes before analysis or use. However, the proteins may instantaneously bind the nanoparticles and little or no incubation may be required. Salts and excess protein, unbound protein, may be washed away from the gold colloids. Washing may be accomplished by centrifuging the samples. For example, the solution may be centrifuged at about 13200 r/min for about 40 min. The supernatant may then be discarded and then water may be added and mixed, by vortex for example, to suspend the colloids.

Upon formation of glycoprotein/colloidal particles in Step 1, either the method of Steps 2 or 3 may be performed, or method of Steps 4 and 5 may be performed, to characterize the composition and/or structure or identify the glycans on the glycoproteins bound to the colloidal particles. Step 2 comprises binding the glycoprotein/colloid formed in Step 1 with a binding agent. In at least one aspect, the binding agent may be selected from the group consisting of sugar binding proteins, nucleic acids, polymeric materials, and combinations thereof. In at least one aspect, the binding agent comprises lectin. In at least one further aspect, WGA, PNA and Jacalin lectin solutions may be prepared at a desired concentration and desired pH. For example, WGA, PNA and Jacalin lectin solutions may be prepared at a concentration of about 60 μg/mL in 2.5 mmol/L sodium tetraborate buffer with 1.5 mmol/L NaCl (pH=9). In at least one aspect, lectin solutions may be made. For example, lectin solutions may be made by dissolving about 1 mg of lectin in 1 mL of 4-(2-hydroxyethyl) piperazine-1-ethanesulfonic acid (HEPES, 99.5%) buffered saline, HBS (pH 7.4, 150 mmol/L NaCl, 0.01 mol/L HEPES, 1 mmol/L $Ca^{2+}$, 1 mmol/L $Mn^{2+}$). In at least one aspect, a final lectin concentration of about 50 μg/mL may be obtained by dilution of the lectin solution in a ratio of about 1:20 (v/v) with the RNase B gold nanoparticle solution, for example. Type I water (UV treated; 18 MΩ·cm; 0.2 micrometer final filter) may be used for solution preparations, for example. A microcentrifuge with a fixed angle rotor may be used for preparation.

In at least one other aspect, the protein may comprise Rituxan® ($C_{6416}H_{9874}N_{1688}O_{1987}S_{44}$). Rituxan® may comprise about 10 mg/mL of antibody, 9 mg/mL of sodium chloride, 7.35 mg/mL of sodium citrate dihydrate, and 0.7 mg/mL polysorbate 80 at pH=6.5, for example. The formulated Rituxan® may be purified by Protein A affinity chromatography, for example. The purified Rituxan® may have a concentration of about 9 mg/mL and may be stored at −18° C. in 25 mmol/L phosphate buffer, pH 7.4, with 0.01% $NaN_3$, for example.

In at least one aspect of Step 1, in FIG. 1, Rituxan®-Au NP conjugates may be prepared by adding about 334 µL of 30 nm Au NPs (~200 pM, pH=9) to 6 µL of 9 mg/mL purified Rituxan® and 160 µL of nanopure water, for example. The dispersion may be allowed to interact for about 1 minute at room temperature using an automatic shaker, for example. The dispersion may then be centrifuged for about 10 minutes at about 10 krpm, for example. After centrifugation, the supernatant may be decanted, and the Rituxan®-Au NP conjugates may then be redispersed in water to a final sample volume of about 500 µL, for example.

For the lectin-based colorimetric assay, equal volumes of Rituxan®-Au NP conjugates and lectin may be mixed and allowed to interact for up to two hours at room temperature with the aid of an automatic shaker. The final lectin concentration may be ≈30 µg/mL. The samples may then be analyzed by UV-visible spectroscopy and Dynamic light scattering (DLS), for example, in Step 3.

In Step 3 the glycoproteins may be characterized and/or the composition and/or structure may be identified with an optical assay or size increase measurement, for example. For example, DLS measurements may be made at about 25° C. Approximately 200 µL of sample may be added to a low-volume disposable cuvette and allowed to equilibrate for about thirty seconds before analysis. Particle sizes (hydrodynamic diameters, DH) may be obtained and reported and may be based on intensity distributions and application of non-negative least squares analysis method. The hydrodynamic diameter values may represent the average of at least three measurements and the standard deviation of the measurement. A detection angle of about 173° may be used for the analyses.

In another aspect, the glycoproteins may be identified with UV-visible absorption analyses, in Step 3. For example, a UV-visible absorption spectra may be measured from 1000 nm to 400 nm at a scan rate of 240 nm/min and a Step size of 1 nm against a water or buffer background sample, for example.

A Fourier transform infrared spectroscopy (FT-IR) spectra of the glycoprotein/colloidal particles may be recorded. At least 512 scans may be collected with a resolution of about 2 $cm^{-1}$ for each sample. Samples may be prepared by depositing 50 µL of the desired sample on a Teflon IR card and left to dry in a laminar flow hood prior to FT-IR measurements.

In another aspect, DLS measurements may be at about 25° C. Approximately 200 µL of sample may be added to a low-volume disposable cuvette and allowed to equilibrate for about one minute before analysis, a minimum of ten runs of ten seconds each may be used, for example. Particle sizes (hydrodynamic diameters) may be reported and may be based on intensity distributions, and the average particle size may be obtained by using a non-negative least squares (NNLS) analysis method. The hydrodynamic diameter and associated errors may be reported in and determined by the average and the standard deviation of at least three measurements, for example.

Figure 3:
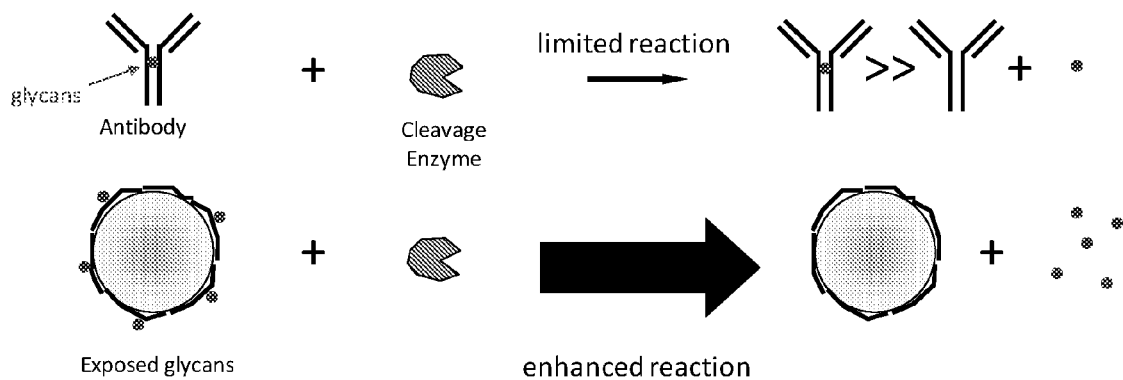
FIG. 3 is a chemical equation of method steps 1 and 4 of the method of the flowchart of FIG. 1 showing the cleaving of oligosaccharides from glycoprotein/colloidal particles.
Figure 4:
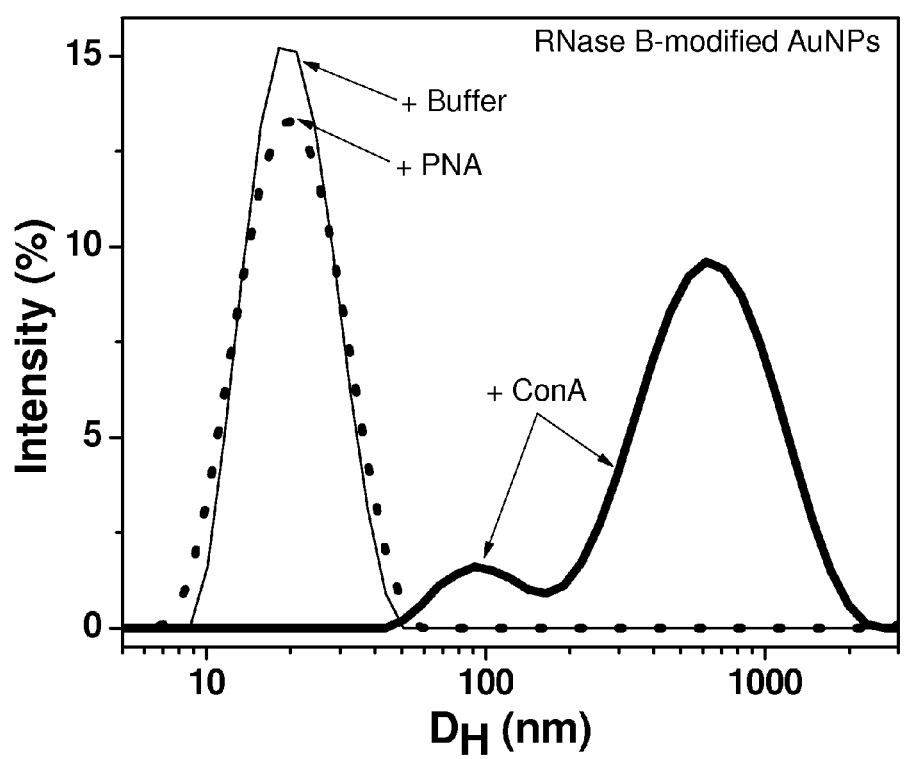
FIG. 4 shows dynamic light scattering results for RNase B-modified gold nanoparticles before (+ buffer) and after the addition of PNA and Con A lectins.
Figure 5:
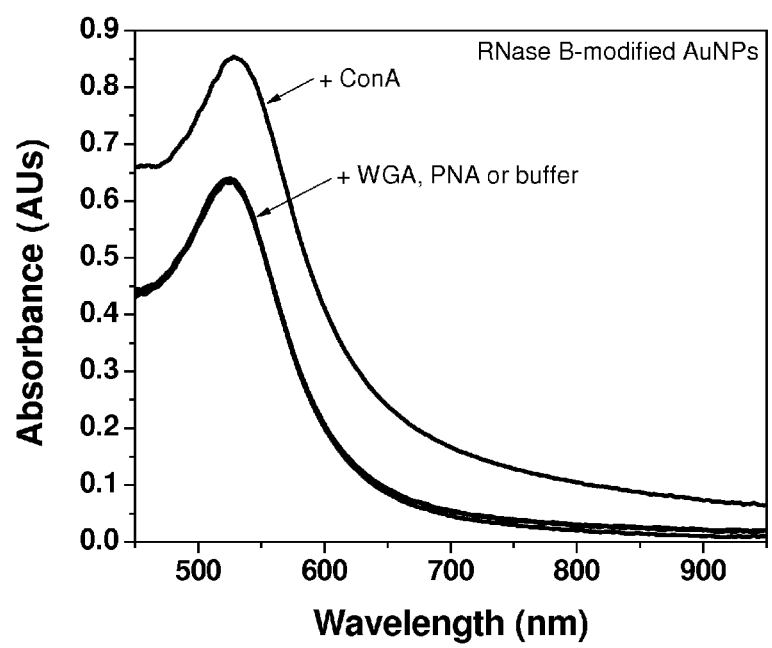
FIG. 5 shows a UV-Vis spectra of RNase B-modified gold nanoparticles acquired approximately 1 min after the addition of Con A, WGA, PNA, or buffer.

Alternatively, glycans or oligosaccharides may be cleaved from the glycoprotein/colloidal particles and analyzed in Steps 4 and 5 of FIG. 1. For example, the colloidal particles may expose the glycans on the surface of the colloidal particles, as shown in FIG. 3, which may enhance cleaving by a cleaving agent such as PNGase F, for example. As shown in FIG. 3, cleaving of the glycans from the glycoprotein/colloidal particles releases at least a portion of the glycans from the glycoprotein. The glycans may then be analyzed by chromatographic or mass spectrometric analysis, for example.

EXAMPLES

Objects and advantages of this invention may be further illustrated by the following examples, but the particular materials and amounts thereof recited in these examples, as well as other conditions and details, should not be construed to unduly limit this invention. For example, selected glycoproteins and selected colloidal particles were used in the following Examples, by way of example only, and their selection shall not be construed to limit the claims herein. One or more examples may be applicable to monoclonal antibody drugs.

Example 1

In this example, a glycoanalysis method wherein lectins are used to directly probe the glycans of glycoproteins that are adsorbed on gold nanoparticles is shown. A model mannose-presenting glycoprotein, ribonuclease B (RNase B), is shown to adsorb to bare gold nanoparticles (≈10 nm in diameter) such that glycans may be accessible for lectin binding. Addition of concanavalin A (Con A), a multivalent mannose-specific lectin, to a solution of the RNase B modified gold nanoparticles may result in cross-linking of the nanoparticles. Cross-linking may occur within 1 minute by a change in the hydrodynamic radius, $D_H$, measured by dynamic light scattering (DLS) and a shift and increase in absorbance of the plasmon resonance band of the gold nanoparticles. The specificity of the assay was confirmed through several controls using two non-mannose-specific lectins (peanut agglutinin and wheat germ agglutinin), inhibitory sugars, and a non-glycosylated version of RNase B (RNase A). RNase B coated gold nanoparticles were characterized using DLS, X-ray photoelectron spectroscopy (XPS), and analytical ultracentrifugation (AUC). In addition, matrix-assisted laser desorption/ionization time of flight mass spectral analysis (MALDI TOF MS) was used to detect the presence of Con A in the aggregated RNase B-modified nanoparticles. This may demonstrate glycan characterization of gold nanoparticle bound glycoproteins using a variety of binding lectins.

Concanavalin A (Con A), wheat germ agglutinin (WGA), and peanut agglutinin (PNA) were purchased from Vector Laboratories of Burlingame, Calif., and used without further purification. Ribonuclease A (RNase A, from bovine pancreas, reagent grade), ribonuclease B (RNase B, from bovine pancreas, >80%), bovine serum albumin, sodium chloride (99.9%), manganese chloride tetrahydrate (99.99%), calcium chloride dihydrate (98%), 4-(2-hydroxyethyl)piperazine-1-ethanesulfonic acid (HEPES, 99.5%), and indium foil (99.99%) were purchased from Sigma-Aldrich of St. Louis, Mo., US, and used as received. Inhibitory sugars, D-mannose (99.9%) and D-(+)-Glucose (99.5%) were used as received. Citrate-stabilized gold nanoparticles (average diameter ≈10 nm) were purchased from Ted Pella, of Redding, Calif., US. The manufacturer reported concentration is $5.7 \times 10^{12}$ particles/mL. Stock lectin solutions were made by dissolving 1 mg of lectin in 1 mL of HEPES buffered saline, HBS (pH 7.4, 150 mmol/L NaCl, 0.01 mol/L HEPES, 1 mmol/L $Ca^{2+}$, 1 mmol/L $Mn^{2+}$). Con A requires trace amounts of $Ca^{2+}$ and $Mn^{2+}$ as co-factors for activity. A final lectin concentration of 50 µg/mL was obtained by dilution of the stock lectin solution in a ratio of 1:20 (v/v) with the RNase B gold nanoparticle solution, as described below. Type I water (UV treated; 18 MΩ·cm; 0.2 micrometer final filter) was used for all solution preparations. A microcentrifuge with a fixed angle rotor (model 5415 D, manufactured by Eppendorf of Hamburg, Germany) was used for preparative centrifugation.

Protein-modified gold nanoparticles were prepared by first dissolving the protein in water at a concentration of 1 mg/mL, a stock concentration that was previously determined to result in saturation of protein coverage by AUC analysis. The pH of the as-received 10 nm gold nanoparticle solution was raised to ≈10 with 0.1 mol/L NaOH, as measured by EMD color-pHast pH test strips, manufactured by EMD Chemicals of Gibbstown, N.J., US. Protein solution was added to the gold nanoparticle solution at a volume ratio of 1:10; the final protein concentration was therefore about 100 μg/mL when mixed with the nanoparticles. The solution was mixed and allowed to incubate at room temperature for at least 30 min before analysis or use.

Dynamic light scattering (DLS) measurements were made with a Malvern Zetasizer Nano ZS DLS system, manufactured by Malvern Instruments of Worcestershire, UK, at about 25° C. Approximately 200 μL of sample were added to low-volume disposable cuvettes and allowed to equilibrate for thirty seconds before analysis. Ten runs of ten seconds each were used to analyze each sample. All particle sizes (hydrodynamic diameters, $D_H$) reported here were based on intensity distributions and were obtained using the non-negative least squares analysis method. The hydrodynamic diameter values reported represent the average of at least three measurements and the standard deviation of the measurement. A detection angle of 173° was used for the analyses.

UV-visible absorption spectra were measured with a with a Lambda Bio 20 spectrophotometer, manufactured by Perkin-Elmer of Waltham, Mass., US, using a 1 cm path length quartz cuvette. The absorption spectrum was measured from 1000 nm to 400 nm at a scan rate of 240 nm/min and a step size of 1 nm against a water or buffer background sample.

X-ray photoelectron spectroscopy (XPS) was performed on a Kratos Axis Ultra$^{DLD}$ instrument, manufactured by Kratos Analytical Limited, Kyoto, Japan, with monochromatic Al Kα radiation (1486.7 eV). Survey scans were obtained for unmodified and RNase B-modified gold nanoparticles in the fixed analyzer transmission mode with pass energy of 160 eV. The binding energies were calibrated with respect to the gold 4f 7/2 peak at 84.0 eV. XPS samples were prepared by first washing away salts and excess protein from the gold colloids by repeatedly centrifuging the samples at 13200 r/min for 40 min, discarding the supernatant, adding water, and mixing by vortex to suspend the colloids. This process was repeated at least twice. A small aliquot (10 μL to 15 μL) of the concentrated colloid was then drop cast and allowed to dry on a clean piece of indium foil for analysis. The number of wash steps necessary were determined by monitoring the Na 1 s signal at ≈1070 eV. For insufficiently washed samples, sodium from NaOH added for pH control was detected by XPS.

Analytical ultracentrifugation (AUC) data was acquired with a Beckman XL-A analytical ultracentrifuge using a 4 place titanium rotor (model An-60 Ti, manufactured by Beckman Coulter, Inc. of Brea Calif., US). Sample cells were outfitted with 12 mm path length dual sector centerpieces, manufactured by Epon™ of Sylmar, Calif. The reference cell was filled with 425 μl of water and the sample cell was filled with 400 μl of either unmodified or RNase B-modified gold nanoparticles. The RNase B-modified gold particles were washed to remove excess salts and protein as was done with the samples for XPS analysis. Run conditions of the AUC for all samples were set as follows: temperature of 20° C.; absorbance wavelength of 520 nm (to correspond with the maximum in the absorption spectrum of the gold particles); scan step size of 0.007 cm; rotation speed of 10000 r/min; and absorbance scan rate of once every 2 min. The raw centrifugation data was converted into sedimentation coefficient distributions using a continuous c(s) distribution model in Sedfit.

Matrix-assisted laser desorption-ionization time-of-flight mass spectrometry (MALDI-TOF MS, manufactured by Applied Biosystems) data were collected in the positive ion and linear modes using a 337 nm nitrogen laser for irradiating samples. Ions generated from 6000 laser pulses were collected and averaged for each spectrum. The matrix solution for all MALDI experiments was prepared by dissolving sinapinic acid (Fisher) at a concentration of 20 mg/mL in a solution of trifluoroacetic acid/acetonitrile/water (0.1:50:50 v/v/v). The sample was mixed with an equal volume of matrix solution. A 0.5 μL aliquot of the resulting solution was spotted onto a MALDI target plate and allowed to air dry prior to analysis.

RNase B is an example of a glycoprotein which demonstrates a lectin-based gold nanoparticle glycan assay. RNase B is a glycoprotein with a N-linked saccharide structure of —(NAG)$_2$Man$_x$ where NAG is N-acetylglucosamine, Man is α-mannose and x is 5 to 9. Although nine compositionally- or structurally-distinct glycoforms are present in commercially-available RNase B, all glycoforms possess α-mannose moieties on the non-reducing end. The oligosaccharide portion of RNase B comprises approximately 10% of the mass of the protein. Therefore, RNase B-modified gold nanoparticles may present α-mannose moieties at a relatively high surface density.

The size distribution of the RNase B-modified gold nanoparticles was established using DLS. The hydrodynamic diameter of the gold nanoparticles as measured by DLS increased from 17.9 nm±0.5 nm before RNase B adsorption to 21.3 nm±0.7 nm after conjugation with RNase B. This increase in hydrodynamic radius of ca. 1.7 nm agreed with the hydrodynamic radius of RNase A, to the non-glycosylated form of RNase B. UV-visible absorbance analysis was also used to evaluate the conjugation of RNase B to the gold nanoparticles. Unmodified 10 nm gold colloids exhibit a characteristic $\lambda_{max}$ absorbance peak at 520 nm due to the surface plasmon resonance of the colloidal gold, whereas the $\lambda_{max}$ value of RNAse B-modified gold colloids shifted to 525 nm. The 5-nm red shift may be due to changes in the refractive index at the gold nanoparticle surface and is consistent with those reported for the adsorption of proteins to colloidal gold.

In addition to the size change and optical evidence of RNase B adsorption, results from X-ray photoelectron spectroscopy (XPS) and analytical ultracentrifugation (AUC) also showed evidence for the adsorption of RNase B to the gold nanoparticles. By XPS analysis, nitrogen was detected in RNase B-modified gold nanoparticle samples but not in unmodified nanoparticles. The presence of N is photoelectrons is unique to the protein-modified nanoparticles and demonstrates that RNase B is adsorbed to the surface of the gold nanoparticle.

Analytical ultracentrifugation (AUC) was used to analyze both unmodified and RNase B-modified gold nanoparticle samples. The sedimentation coefficient of RNase B-modified gold nanoparticles was found to be lower than for unmodified gold nanoparticles. This may be because the adsorption of RNase B may reduce the overall density of the nanoparticle conjugate, increasing the buoyancy of the particle and resulting in a lower sedimentation coefficient.

To determine the optimal concentration for glycoprotein adsorption, the sedimentation coefficient was determined for stock concentrations of RNase B varying from 0.25 mg/mL to 2 mg/mL at a constant concentration of gold nanoparticles.

The sedimentation coefficient decreased with increasing stock RNase B concentration until reaching a minimum value at 1.0 mg/mL. The sedimentation coefficient distribution remained constant at stock RNase B concentrations above 1.0 mg/mL, indicating that the maximum surface coverage of RNase B was attained at that stock concentration. Since the RNase B stock solution is mixed in a 1:10 v/v ratio with the gold nanoparticle solution, the final RNase B concentration is 100 μg/mL when mixed with the nanoparticles. Finally, multiple washing of RNase B-modified particles with buffer resulted in little change to the AUC determined sedimentation coefficient suggesting largely irreversible adsorption of RNase B to the gold nanoparticle surface.

The interaction of the lectin Con A with the RNase B-modified gold nanoparticles was examined because it binds specifically to mannose and its interaction with RNase B has been well-studied. For the solution conditions used in this example (pH 7.4), Con A exists as a tetramer with four independent sugar binding sites.

To demonstrate that the specific binding of the lectin causes the observed change in surface plasmon resonance, two non-mannose specific lectins, peanut agglutinin (PNA) and wheat germ agglutinin (WGA), were also introduced to the RNase B-modified gold nanoparticles in separate control experiments. PNA and WGA are multivalent lectins specific for galactose and N-acetylglucosamine respectively. Because PNA and WGA have low affinity for the glycans of RNase B, these lectins may not induce aggregation of the RNase B-modified gold nanoparticles. A buffer control was also used to ensure that aggregation was not induced by changes in concentration; pH and ionic strength were maintained in all test solutions.

The addition of a Con A solution to RNase B-modified gold nanoparticles resulted in changes to the nanoparticle size distribution as measured by DLS as shown in FIG. 4. The hydrodynamic diameter of the RNase B-modified gold nanoparticles increased on average from 21.3 nm±0.7 nm to a multimodal distribution with peaks observed at 90 nm±10 nm and 660 nm±50 nm approximately one minute after addition of Con A. These data are consistent with the illustration of FIG. 2. The bimodal distribution may be attributed to a mixture of multimers of aggregated nanoparticles and larger aggregate species. No significant increase in the average hydrodynamic diameter was observed for the RNase B-modified gold nanoparticles upon addition of the non-binding PNA lectin (hydrodynamic radius of 20 nm±1 nm, FIG. 4).

Evidence for aggregation upon introduction of Con A to RNase B-modified gold nanoparticle samples was also provided by analysis of an UV-visible spectrum that was acquired approximately 1 minute after mixing (FIG. 5). The final concentration of lectins in all cases was 50 μg/mL. Specifically, the absorbance at all wavelengths increased and the plasmon band shifted to the red by 4 nm to 529 nm. These spectral changes were also discernable by eye as a decrease in transparency and a color change to red-purple. In contrast, addition of either of the non-mannose specific lectins, PNA or WGA, caused no change to the absorption spectrum.

The red-shift of the plasmon band of the RNase-B modified gold nanoparticles after addition of Con A may be due to increased interparticle plasmon coupling due to aggregation. As illustrated in the FIG. 2, these aggregates likely consist of two or more gold nanoparticles, separated by a protein tri-layer (RNase B/Con A/RNase B). The distance between the RNase B/Con A/RNase B gold nanoparticle agglomerates can be estimated by the magnitude of the red-shift and the "plasmon ruler equation" to be ca. 7 nm. This distance corresponds well with a reasonable estimate of the protein tri-layer thickness obtained by summing the thickness of the adsorbed RNase B protein layer (ca. 1.5 nm from DLS) and the reported size of a Con A tetramer (ca. 3 nm to 7.5 nm depending on orientation).

MALDI-TOF MS was used also used to confirm the presence of Con A in an aggregated sample of RNase B-modified gold nanoparticles exposed to Con A. After thorough rinsing to remove excess RNase B and Con A from the sample, peaks characteristic of Con A and RNase B were observed, providing further evidence that Con A is bound to the RNase-B modified gold nanoparticles.

After addition of Con A, the UV-Vis absorption spectra of the RNase B-modified gold nanoparticles were monitored over the course of a few hours (FIG. 6). The absorbance band decreases over time as the nanoparticle aggregates sediment to the bottom of the assay vessel. In contrast, the addition of either WGA or PNA to the RNase B-modified gold nanoparticles resulted in no change to the absorbance spectrum over the same period. FIG. 6 also shows a plot of the absorbance maxima of the RNase B-modified gold nanoparticle samples exposed to Con A, WGA, PNA or buffer measured at 15 min intervals from 1 min to 150 min after mixing. Ninety minutes after the introduction of Con A the absorbance at all wavelengths decreased as the aggregated particles sedimented to the bottom of the cuvette and out of the path of the sampling light. In contrast, the introduction of WGA (or PNA) did not significantly affect the optical properties or stability of the RNase B-modified gold nanoparticles.

Rapid results that are discernable by eye, not requiring analytical instrumentation (e.g. a DLS or spectrophotomer), may be achieved with the assay by using mild centrifugation. Moderate centrifugation (3000 r/min for 5 min) caused the aggregated particles to sediment to the bottom of a centrifuge tube, leaving a clear, colorless supernatant, observable by eye. In contrast, control mixtures using WGA and PNA, centrifuged identically were indistinguishable by eye to non-centrifuged suspensions of RNase B coated gold nanoparticles.

To further show that the optical changes observed for the RNase B-modified gold nanoparticles exposed to Con A may be caused by specific lectin-oligosaccharide cross-linking of the particles, two additional control tests were performed. The first used inhibitory sugars to compete with lectin-glycan binding and the second used a non-glycosylated form of RNase B, RNase A.

Mannose and glucose are commonly used to elute glycoproteins purified from Con A agarose bead chromatographic columns. One may expect that the addition of an excess of these inhibitory sugars, the Con A sugar binding sites would be occupied and no change in the RNase B-modified gold nanoparticle suspension may be observed. The inhibitory sugar mixture of equal parts mannose and glucose was added to the Con A solution at a concentration of 500 mmol/L and incubated overnight. The Con A solution was then added to the RNase B modified-gold nanoparticles and the absorbance spectrum was measured after 1 min (FIG. 7*a*). This absorption spectrum was indistinguishable from the buffer-diluted RNase B-modified gold nanoparticles suggesting that the sugars effectively competed for binding with Con A versus the mannose-presenting groups of the RNase B-modified gold nanoparticle suspension. These data indicate that Con A may bind specifically to the mannose-presenting groups and may be responsible for aggregation of the RNase B-modified gold nanoparticles.

The amino acid sequence of RNase A is substantially identical to RNase B; however, RNase A is non-glycosylated. The RNase A-modified gold nanoparticles were prepared following the same procedure for preparing RNase B-modified gold nanoparticles and the UV-Vis experiments were repeated. No discernable change in the UV-Vis spectra was observed following addition of Con A or the other control species (PNA and WGA) to the RNase A-modified gold nanoparticles (FIG. 7B), this was observed even after 150 minutes. Based on this result and the experimental results described above, the change in the measured nanoparticle plasmon absorbance and aggregation may be mediated by specific lectin-oligosaccharide interactions between Con A and the mannose presenting groups of RNase B.

To probe the sensitivity of the assay, the relative amount of RNase B adsorbed to each gold nanoparticle was controlled by varying the relative mole fraction of RNase B to RNase A during the adsorption to the gold nanoparticles. During the glycoprotein adsorption step, the total glycoprotein solution concentration was maintained at 100 µg/mL and the molar composition of RNase B to RNase A was varied from 0 to 100%. Absorbance spectra for RNase B-modified gold nanoparticles at different mole ratios acquired approximately 1 minute after introduction of Con A are shown in FIG. 8A. The $\lambda_{max}$ absorbance values increase with higher mol percent RNase B. A plot of the change in absorbance at $\lambda_{max}$ vs. mole % RNase B illustrates this trend (FIG. 8B). An evident change in absorbance is observed at solution concentrations of RNase B as low as 1 µg/mL (FIG. 8A, 0% and 1% lines) after addition of Con A. A linear response was observed for solution concentrations of RNase B below 5 µg/mL and no further change in absorbance was observed at concentrations above 20 µg/mL.

This example may demonstrate a rapid glycoanalysis method by Con A binding to RNase B-modified gold nanoparticles using either a simple instrumentation (e.g. DLS or spectrophotometry) within 1 min after mixing or by visual inspection after mild centrifugation (5 min). An advantage of this method over more conventional glycoanalysis methods may be its simplicity. This method may be used to interrogate unknown glycoproteins or as a qualitative, fingerprinting method using multiple binding lectins for assessing changes in the glycoprofile of a well-characterized glycoprotein. The method demonstrated herein may have an application of the assay to glycoprotein therapeutics, such as monoclonal antibodies, where the glycoprofile of these products must be consistent for each batch manufactured to help ensure drug efficacy and safety.

Example 2

Herein we show dynamic light scattering (DLS) and UV-visible spectroscopy data to demonstrate that the glycans of the monoclonal antibody (mAb) Rituxan® adsorbed on gold nanoparticles (Au NPs) are well-presented and accessible to interact with the appropriate lectin, and that multivalent binding between lectins and the presented glycans induced aggregation of the mAb-modified Au NPs.

This example shows a mAb glycan screening assay using gold nanoparticles (Au NPs). Rituxan®-Au NP conjugates were prepared by mixing Rituxan® and 30 nm Au NPs at pH 9 for one minute, followed by centrifugation, decanting of solution, and re-dispersion in water to remove excess Rituxan®. Basic conditions were used to prepare the Rituxan®-Au NP conjugates since they may exhibited greater stability, i.e., a lower propensity to flocculate. A minimum concentration of 0.1 mg/mL Rituxan® was required to stabilize the Au NPs, which was determined from salt-induced flocculation tests. The adsorption of Rituxan® to Au NPs was confirmed by DLS, where the measured diameter increased from (26+3) nm for the bare Au NPs to (58+4) nm after conjugation with Rituxan®. Rituxan®-Au NP conjugate solutions prepared in this way exhibited a red-pink color. Adsorption of Rituxan® to Au NPs was irreversible over a 24 hour period as no change in size was observed by DLS for particles suspended in pure buffer solution. Further evidence for conjugation was provided by the presence of protein amide I and amide II bands in the Fourier-transform infrared spectrum of Rituxan® modified Au NPs.

DLS and UV-visible spectroscopy were performed one minute and two hours after introduction of the lectins to monitor lectin-induced aggregation of the Rituxan®-Au NP conjugates. Wheat Germ Agglutinin (WGA) was examined as a potential binding lectin due to its affinity for N-acetylglucosamine (GlcNAc) residues. Evidence for binding and aggregation of the Rituxan®-modified Au NPs with the addition of WGA was observed by an increase in hydrodynamic diameter (DH) of the conjugates by DLS, as well as by the changes in the UV-visible spectra. DLS data shows that the hydrodynamic diameter of the Rituxan®-Au NP conjugates increased from (58±4) nm to (430±70) nm after addition of WGA, suggesting that binding of WGA to GlcNAc residues of the mAb results in aggregation of the mAb-Au NP conjugates (FIG. 10A: (a) DLS diameter results for the Rituxan®-Au NP conjugates before (a) and two hours after the addition of PNA (b), WGA (c) and WGA/GlcNAc (d).). The addition of another lectin expected to bind to the glycans of Rituxan®, Con A, a mannose-binding lectin, caused a similar increase in diameter. Changes in the UV-visible spectra of the mAb Au NP conjugates after addition of WGA also suggest aggregation of the conjugates due to lectin-glycan binding (FIG. 10B: UV-visible spectra of Rituxan®-Au NP conjugates after two hours in buffer (solid line) and in the presence of PNA (dashed line) and WGA (dotted line)). The plasmon resonance band of well-dispersed Rituxan®-Au NP conjugates has an absorbance maximum at 534 nm. Two hours after addition of WGA, a broadening and red-shift in the plasmon resonance band was observed, thus corroborating DLS results. Furthermore, after 24 hours in the presence of WGA or Con A, solutions of the Rituxan®-Au NP conjugates turned from red pink to clear due to sedimentation of aggregates.

Several control experiments were performed to verify that the specific lectin-glycan interaction caused the observed spectral changes. First, the effect of adding two lectins that may have low affinity for the glycans of the Rituxan®-Au NP conjugates was examined. Peanut agglutinin (PNA) and Jacalin, multivalent lectins with high specificity for β-D-Gal(1-3)-D-GalNAc residues, may exhibit little affinity for the glycans of Rituxan®. As expected, no significant increase in diameter was observed using DLS after the addition of the non-binding control lectins, PNA, (61±5) nm, as shown in FIG. 10A (b), or Jacalin lectin, (52±7) nm (data not shown). Similarly, no significant changes in the UV-visible spectra of the NPs were observed when either PNA (FIG. 10B) or Jacalin (data not shown) was added. Even after 24 hours in the presence of PNA or Jacalin, the Rituxan®-Au NP conjugates appeared stable as evidenced by their characteristic red-pink color.

In another control experiment, the effect of adding WGA previously incubated with an excess of GlcNac to the Rituxan®-Au NP conjugates, was examined. GlcNAc is a sugar which may be expected to compete with glycan-WGA binding, and, thus, inhibit cross-linking of Rituxan®-Au NP conjugates. As shown by DLS data in FIG. 10A (d), although a slight 10 nm increase in diameter was observed, the presence of free GlcNAc inhibits the formation of large aggregates.

Taken together, these data support that aggregation of the Rituxan®-Au NP conjugates upon addition of WGA and Con A results from specific interactions between the glycans of the immobilized mAb and the binding lectin.

The assay data presented were obtained two hours after addition of the lectins to the Rituxan®-Au NP conjugates. These long assay times are a consequence of the pH used for the conjugation of Rituxan® to the Au NPs. Although the stability of the Rituxan®-Au NP conjugates may be higher under basic conditions (pH 9), lectin binding may be enhanced at neutral pH values. By lowering the pH to neutral, it was shown that the assay may be performed in as little as one minute. Approximately one minute after addition of WGA, an increase in DH of ca. 13 nm, as measured by DLS, was observed with the addition of WGA, but not with the addition of the non-binding lectins PNA and Jacalin (FIG. 11A: DLS diameter results for the Rituxan®-Au NP conjugates before (a) and approximately one minute after the addition of PNA (b), Jacalin (c) and WGA (d)). Similarly, a reproducible increase in absorbance and red-shift of ca. 4 nm was observed in the plasmon resonance band of the Rituxan®-Au NP conjugates (FIG. 11B) one minute after addition of WGA. These variations may be due to changes in the local refractive index around the Au NPs from lectin binding to the oligosaccharides of the Rituxan®-Au NP conjugates or to scattering effects induced by the formation of aggregates. No such changes were observed upon dilution with buffer or when the non-binding lectins PNA or Jacalin were added to the conjugates.

This example shows a method of a lectin-based nanoparticle assay for oligosaccharide screening of therapeutic mAbs. The simplicity of the conjugation method in combination with the convenience of the detection of the lectin-induced aggregation of the NPs by DLS or UV-visible spectroscopy may aid in the development of rapid and simple antibody glycosylation assays.

The invention claimed is:

1. A method of characterizing glycans attached to glycoproteins comprising the steps of:
   a) spontaneously immobilizing said glycans attached to glycoproteins on colloidal particles forming glycoprotein/colloidal particles;
   b) optically assessing the glycoprotein/colloidal particles or measuring their size;
   c) aggregating said glycoprotein/colloidal particles with a binding agent forming an aggregate;
   d) optically assessing the aggregate or measuring a size increase by comparing the assessment of the aggregate with the assessment of said glycoprotein/colloidal particles; and
   e) characterizing the composition or structure of said glycans.

2. The method of characterizing glycans attached to glycoproteins of claim 1 wherein said glycoproteins are selected from the group consisting of polyclonal antibodies, monoclonal antibodies, and combinations thereof.

3. The method of characterizing glycans attached to glycoproteins of claim 1 wherein said colloidal particles are selected from the group consisting of gold, silver, core-shell, polystyrene, carbon nanotubes, and combinations thereof.

4. The method of characterizing glycans attached to glycoproteins of claim 1 wherein said colloidal particles have an average size of less than 1000 nanometers in at least one dimension.

5. The method of characterizing glycans attached to glycoproteins of claim 1 wherein said binding agent is selected from the group consisting of sugar binding proteins, nucleic acids, polymeric materials, and combinations thereof.

6. The method of characterizing glycans attached to glycoproteins of claim 1 wherein said method step b) further comprises:
   placing separate aliquots of said glycoprotein/colloidal particles into separate wells of a microtiter plate; and
   binding said glycoprotein/colloidal particles with different said binding agents in each said separate well of said microtiter plate.

7. The method of characterizing glycans of claim 1 wherein said colloidal particles comprise at least a portion selected from the group consisting of gold, silver, core-shell, polystyrene, carbon nanotubes, and combinations thereof.

8. The method of characterizing glycans of claim 7 wherein said colloidal particles comprise gold nanoparticles.

9. The method of characterizing glycans of claim 8 wherein said gold nanoparticles have an average size of less than 1000 nm in at least one dimension.

10. The method of characterizing glycans attached to glycoproteins of claim 1 wherein said binding agent comprises at least one binding agent selected from the group consisting of sugar binding proteins, nucleic acids, and polymeric materials.

11. The method of characterizing glycans attached to glycoproteins of claim 1 wherein said glycoproteins comprise at least one glycoprotein selected from the group consisting of polyclonal antibodies, monoclonal antibodies, and combinations thereof.

12. The method of characterizing glycans of claim 1 wherein said step of immobilizing said glycoproteins on colloidal particles forming glycoprotein/colloidal particles comprises adding at a concentration of about 1 mL of said glycoproteins with about each 100 µg of said colloidal particles.

13. The method of characterizing glycans of claim 12 wherein said step of immobilizing said glycoproteins on colloidal particles forming glycoprotein/colloidal particles comprises forming said glycoprotein/colloidal particles within about 1 minute upon adding said glycoproteins with said colloidal particles.

* * * * *